United States Patent
Samuel et al.

(10) Patent No.: US 10,242,130 B2
(45) Date of Patent: Mar. 26, 2019

(54) SYSTEM, METHOD AND COMPUTER PROGRAM PRODUCT FOR WELLBORE EVENT MODELING USING RIMLIER DATA

(71) Applicants: Landmark Graphics Corporation, Houston, TX (US); Robello Samuel, Houston, TX (US); Olivier Roger Germain, Houston, TX (US)

(72) Inventors: Robello Samuel, Houston, TX (US); Olivier Roger Germain, Houston, TX (US)

(73) Assignee: Landmark Graphics Corporation, Houston, TX (US)

( * ) Notice: Subject to any disclaimer, the term of this patent is extended or adjusted under 35 U.S.C. 154(b) by 646 days.

(21) Appl. No.: 14/435,404

(22) PCT Filed: Nov. 5, 2012

(86) PCT No.: PCT/US2012/063555
§ 371 (c)(1),
(2) Date: Apr. 13, 2015

(87) PCT Pub. No.: WO2014/070207
PCT Pub. Date: May 8, 2014

(65) Prior Publication Data
US 2015/0234954 A1    Aug. 20, 2015

(51) Int. Cl.
| | | |
|---|---|---|
| G06F 17/50 | (2006.01) | |
| E21B 44/00 | (2006.01) | |
| G06F 17/18 | (2006.01) | |
| G06K 9/62 | (2006.01) | |
| G01V 1/50 | (2006.01) | |
| G01V 1/48 | (2006.01) | |
| G06F 16/35 | (2019.01) | |
| G06F 16/2455 | (2019.01) | |

(52) U.S. Cl.
CPC .......... *G06F 17/5009* (2013.01); *E21B 44/00* (2013.01); *G06F 17/18* (2013.01); *G06K 9/6221* (2013.01); *G06K 9/6284* (2013.01); *G01N 2291/02818* (2013.01); *G01V 1/48* (2013.01); *G01V 1/50* (2013.01); *G06F 16/24565* (2019.01); *G06F 16/355* (2019.01)

(58) Field of Classification Search
CPC .............................. G06F 17/5009; G06F 17/18
See application file for complete search history.

(56) References Cited

U.S. PATENT DOCUMENTS

| | | |
|---|---|---|
| 5,444,619 A | 8/1995 | Hoskins |
| 6,392,409 B1 | 5/2002 | Chen |
| 7,983,885 B2 | 7/2011 | Suarez-Rivera et al. |
| 2002/0050989 A1* | 5/2002 | Sanstrom ................ E21B 44/00 345/419 |

(Continued)

OTHER PUBLICATIONS

Cateni et al., Outlier Detection Methods for Industrial Applications, Advances in Robotics, Automation and Control, Jesus Aramburo and Antonio Ramirez Trevino, Available from: http://www.intechopen.com/books/advances_in_robotics_automation_and_control/outlier_detection_methods_for_industrial_applications.

(Continued)

*Primary Examiner* — Kibrom K Gebresilassie
(74) *Attorney, Agent, or Firm* — Haynes and Boone, LLP (57) ABSTRACT

A data mining and analysis system which analyzes clusters of outlier data (i.e., rimliers) to detect and/or predict downhole events.

27 Claims, 5 Drawing Sheets

(56) References Cited

U.S. PATENT DOCUMENTS

| | | | |
|---|---|---|---|
| 2002/0183930 A1* | 12/2002 | Plona | G01V 1/50 |
| | | | 702/6 |
| 2004/0186833 A1* | 9/2004 | Watts | G06F 17/3071 |
| 2006/0001955 A1* | 1/2006 | Kinney | G02B 7/38 |
| | | | 359/391 |
| 2006/0081412 A1 | 4/2006 | Wright et al. | |
| 2006/0162962 A1 | 7/2006 | Koederitz et al. | |
| 2006/0230018 A1 | 10/2006 | Grichnik et al. | |
| 2009/0260883 A1 | 10/2009 | Suarez-Rivera et al. | |
| 2011/0066390 A1 | 3/2011 | Macleod et al. | |
| 2011/0091078 A1 | 4/2011 | Kherroubi et al. | |
| 2012/0118637 A1* | 5/2012 | Wang | E21B 44/00 |
| | | | 175/24 |

OTHER PUBLICATIONS

Gupta et al., Better Drilling Through Sensor Analytics: A Case Study in Live Operational Intelligence, Sensor KDD, Aug. 21, 2011, 8 pages.

International Search Report and the Written Opinion of the International Searching Authority, or the Declaration, dated Jan. 22, 2013, PCT/US2012/063555, 7 pages, ISA/US.

Extended European Search Report for EP 12887689, 6 pages, dated May 20, 2016.

* cited by examiner

SYSTEM, METHOD AND COMPUTER PROGRAM PRODUCT FOR WELLBORE EVENT MODELING USING RIMLIER DATA

The present application is a U.S. National Stage patent application of International Patent Application No. PCT/US2012/063555, filed on Nov. 5, 2012, the benefit of which is claimed and the disclosure of which is incorporated herein by reference in its entirety.

FIELD OF THE INVENTION

The present invention relates generally to data mining and analysis and, more specifically, to a system which analyzes one or more clusters of outlier wellbore data, or "rimliers," to model downhole events.

BACKGROUND

In the past, data mining has been proposed to predict wellbore events. Traditionally, after data extraction, the outlier data is removed to make the data homogeneous because, in order to perform the computations necessary to model the data, the system implicitly assumes that the data is homogeneous and of good quality. Thus, if the outlier data were not removed, conventional time series models, such as Arima, Support Vector Machine, etc., would fail in the drilling domain since they cannot process the outlier data, which can be considered as undesirable noise that would deviate statistical results. Once the outlier data has been removed, the cleaned dataset is then utilized to predict events based on a pattern or trend.

However, the traditional method has disadvantages. Primarily, the removed outlier data may give more insight into past, present or future downhole events such as, for example, bit failure, tool failure due to vibration, etc. Instead of representing noise, the removed outlier data may actually be representative of micro-events of lesser frequency. As such, by removing the outlier data, critical data giving insight into downhole events may be overlooked.

Accordingly, there is a need in the art for system which utilizes the outlier data to detect and predict wellbore events, thereby harnesses all data available downhole data.

DESCRIPTION OF ILLUSTRATIVE EMBODIMENTS

Illustrative embodiments and related methodologies of the present invention are described below as they might be employed in a system to model downhole events using rimlier data. As used herein, "modeling" the downhole events refers to detecting and/or predicting the downhole events. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

Figure 1:
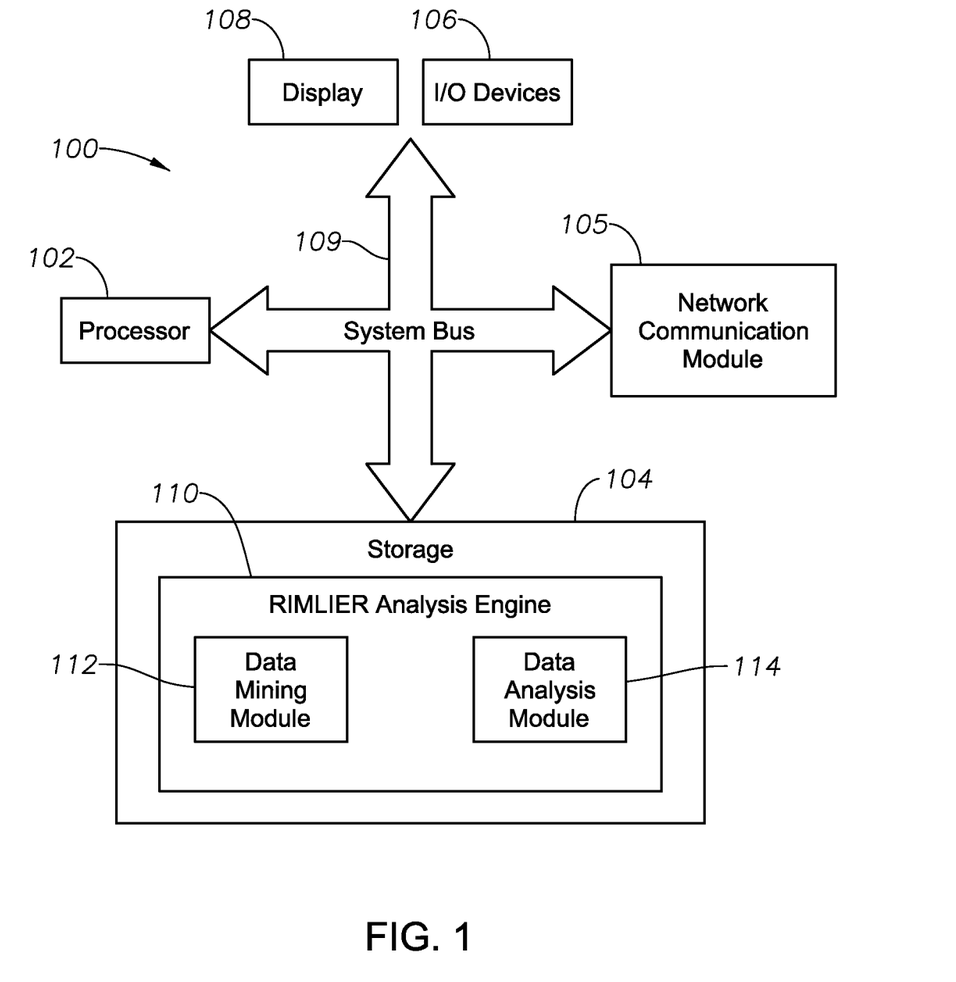
FIG. 1 illustrates a block diagram of a rimlier data analysis system according to an exemplary embodiment of the present invention.

FIG. 1 shows a block diagram of rimlier data analysis system 100 according to an exemplary embodiment of the present invention. As will be described herein, rimlier data analysis system 100 analyzes a group, also referred to herein as cluster, of outlier data showing abnormal behavior, referred to herein as "rimliers." Once identified, rimlier data analysis system 100 analyzes the rimliers to determine those data variables within the rimliers that indicate the occurrence of a downhole event. Then, based upon this analysis, rimlier data analysis system 100 models (i.e., detect and/or predict) downhole events such as, for example, those events typically characterized by transient erratic behavior such as ones caused by tool vibrations, the failure of bearings in the case of roller cone bits, bit or hole opener teeth failure, increased cuttings bed, whirling of bottomhole assembly, etc.

The data analyzed by rimlier data analysis system 100 may be real-time data or stored in a local/remote database. The database may include, for example, general well and job information, job level summary data, pumping schedule individual stage data, or other data typically captured in daily operations reports to indicate operational progress and the overall state of the well. Such data may include, for example, final casing string components and its set depth, ongoing drill string, bottomhole drilling assembly and drill bit used to drill the hole and its size, etc. Exemplary embodiments of the present invention access the database to extract one or more desired datasets. The system then analyzes the dataset for variables indicating patterns or trends and, thus, determines the normal data points and those that deviate from the normal data points, also known as outliers.

Thereafter, rimlier data analysis system 100 groups the outliers, using known statistical mining techniques, and segregates them into low density outlier clusters and high density outlier clusters. As used herein, clustering refers not only to traditional clustering techniques such as, for example, Kernel K-means clustering, but also to other grouping techniques such as, for example, manual visual identification and more advanced computational techniques, as will be understood by those ordinarily skilled in the art having the benefit of this disclosure. Low density outlier clusters are those clusters having a low number of data points, while high density outlier clusters are those which have a higher number of data points. Those ordinarily skilled in the art having the benefit of this disclosure realize that the determination of which clusters are considered high and low density is contingent on the total number of data points in a given outlier dataset. For example, in some instances, a 100 data point outlier cluster may not reflect an actual downhole problem; but, may instead reflect an electrical signal spike. In another example, a 10 data point outlier cluster may reflect an actual downhole issue and, thus, be considered a high density cluster. Nevertheless, as will be described herein, rimlier data analysis system 100 then analyzes the high density outlier cluster, or rimlier, to model downhole events.

Referring to FIG. 1, rimlier data analysis system 100 includes at least one processor 102, a non-transitory, computer-readable storage 104, transceiver/network communication module 105, optional I/O devices 106, and an optional display 108 (e.g., user interface), all interconnected via a system bus 109. Software instructions executable by the processor 102 for implementing software instructions stored within rimlier analysis engine 110 in accordance with the exemplary embodiments described herein, may be stored in storage 104 or some other computer-readable medium.

Although not explicitly shown in FIG. 1, it will be recognized that rimlier data analysis system 100 may be connected to one or more public and/or private networks via one or more appropriate network connections. It will also be recognized that the software instructions comprising rimlier analysis engine 110 may also be loaded into storage 104 from a CD-ROM or other appropriate storage media via wired or wireless communication methods.

Moreover, those skilled in the art will appreciate that the present invention may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present invention. The invention may be practiced in distributed-computing environments where tasks are performed by remote-processing devices that are linked through a communications network. In a distributed-computing environment, program modules may be located in both local and remote computer-storage media including memory storage devices. The present invention may therefore, be implemented in connection with various hardware, software or a combination thereof in a computer system or other processing system.

Still referring to FIG. 1, in certain exemplary embodiments, rimlier analysis engine 110 comprises data mining module 112 and data analysis module 114. Rimlier analysis engine 110 provides a technical workflow platform that integrates various system components such that the output of one component becomes the input for the next component. In an exemplary embodiment, data mining and analysis engine 110 may be, for example, the AssetConnet™ software platform commercially available through Halliburton Energy Services Inc. of Houston, Tex. As understood by those ordinarily skilled in the art having the benefit of this disclosure, database mining and analysis engine 110 provides an integrated, multi-user production engineering environment to facilitate streamlined workflow practices, sound engineering and rapid decision-making. In doing so, rimlier analysis engine 110 simplifies the creation of multi-domain workflows and allows integration of any variety of technical applications into a single workflow. Those same ordinarily skilled persons will also realize that other similar workflow platforms may be utilized with the present invention.

Serving as the database component of rimlier analysis engine 110, data mining module 112 is utilized by processor 102 to capture well related datasets for computation from a server database (not shown) or from real-time downhole data. In certain exemplary embodiments, the server database may be, for example, a local or remote SQL server which includes data variables related to well job details, wellbore geometry data, pumping schedule data per stage, post job summaries, bottom-hole information, etc. In another exemplary embodiment, data mining module 112 receives real-time data from downhole sources using methodologies known in the art. As will be described herein, exemplary embodiments of the present invention utilize data mining module 112 to capture key variables from the database or downhole data source corresponding to different job IDs using server queries. After the data is extracted or received, rimlier analysis engine 110 communicates the dataset to data analysis module 114.

Data analysis module 114 is utilized by processor 102 to analyze the data extracted by data mining module 112. An exemplary data analysis platform may be, for example, Matlab®, as will be readily understood by those ordinarily skilled in the art having the benefit of this disclosure. As described herein, rimlier data analysis system 100, via data analysis module 114, analyzes the dataset to identify rimliers that are used to model downhole events.

Figure 2A:
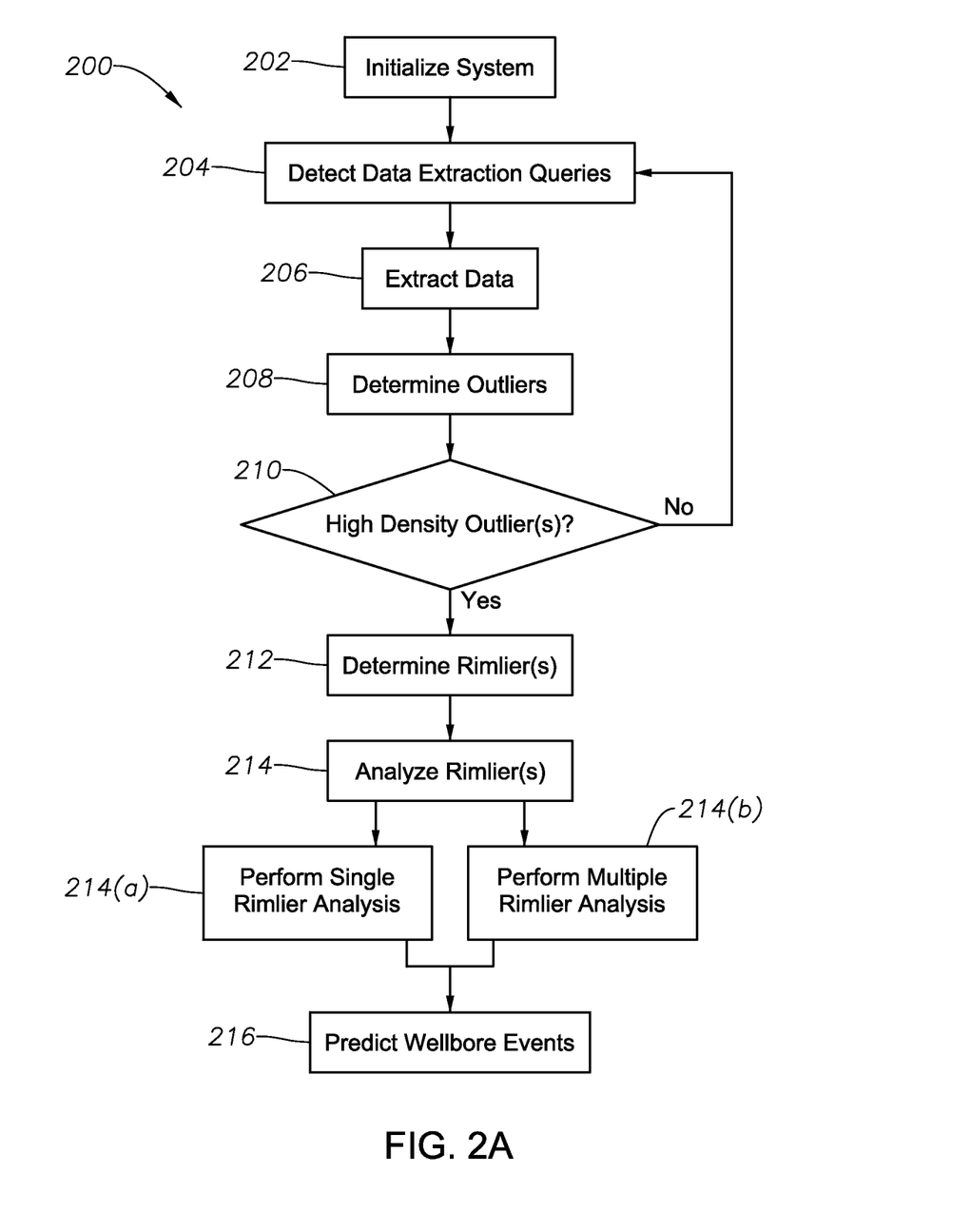
FIG. 2A is a flow chart of a method performed by a rimlier data analysis system according to an exemplary methodology of the present invention.

Now referring to FIG. 2A, an exemplary methodology 200 performed by the present invention will now be described. In this exemplary methodology, rimlier data analysis system 100 analyzes one or more clusters of outlier data, or rimliers, to identify those data variables that indicate one or more downhole events and, thereafter, models those downhole events. For example, rimlier data analysis system 100 may be utilized to detect and/or predict if a particular job has or will experience a screen-out, damaging vibration event, bit failure, etc. As such, the following methodology will describe how rimlier data analysis system 100 mines and analyzes the data to model such downhole events.

At block 202, rimlier data analysis system 100 initializes and displays a graphic user interface via display 108, the creation of which will be readily understood by ordinarily skilled persons having the benefit of this disclosure. Here, rimlier data analysis system 100 awaits entry of queries reflecting dataset extraction. In one exemplary embodiment, SQL queries may be utilized to specify the data to be extracted from the database, while log-extract queries are utilized to upload data from real-time sources. Such queries may include, for example, field location, reservoir name, name of the variables, further calculations required for new variables, etc. At block 204, rimlier data analysis system 100 detects the queries and, at block 206, processor 102 instructs data mining module 112 to extract the corresponding dataset(s) from the database or real-time source. Exemplary dataset variables may include, for example, data points related to weights, pressures, temperatures, vertical or rotary speed, slurry volume, proppant mass, etc., for a particular well. In exemplary embodiments, the signal noise may be eliminated when dual sensors are present that complement the data, as would be understood by those ordinarily skilled in the art having the benefit of this disclosure.

At block 208, rimlier analysis engine 110 analyzes the extracted dataset to determine the outliers. To do so, rimlier analysis engine 110 will analyze the data based upon a given threshold. In certain exemplary embodiments, variables may be assigned outlier status if they are characterized as values greater than three times the standard deviation, although other merit factors may be utilized. Those variables within the threshold are considered normal, while those data points outside the threshold are considered to be outliers. For example, if the extracted dataset related to downhole pressures, those pressures within a certain range would be considered normal, while those outside that range would be considered as outliers. Once the outliers are determined, rimlier analysis engine 110 then groups the outliers using a clustering technique such as, for example, Kernel K-means clustering. However, other clustering techniques may be utilized as would be understood by those ordinarily skilled in the art having the benefit of this disclosure.

In certain exemplary embodiments, rimlier analysis engine 110 may preprocess the extracted data before determining the outliers in order to remove corrupted data. At times, the data entered into the database may comprise incomplete or inconsistent data. Incomplete data may include NAN or NULL data, or data suffering from thoughtless entry. Noisy data may include data resulting from faulty collection or human error. Inconsistent data may include data having different formats or inconsistent names.

At block 210, rimlier analysis engine 110 analyzes the clusters to determine whether there are any high density clusters. As previously described, those ordinarily skilled in the art having the benefit of this disclosure will realize that the determination of which clusters are considered high and low density is contingent on the total number of data variables in a given outlier dataset. For example, 2 data points may be considered high density for an outlier cluster having 10 total variables, while 200 variables may be considered low density for a outlier cluster having 1000 variables. Therefore, certain exemplary embodiments of rimlier analysis engine 110 may make this determination, for example, based upon a pre-defined threshold or a threshold entered dynamically via the user interface.

Figure 2B:
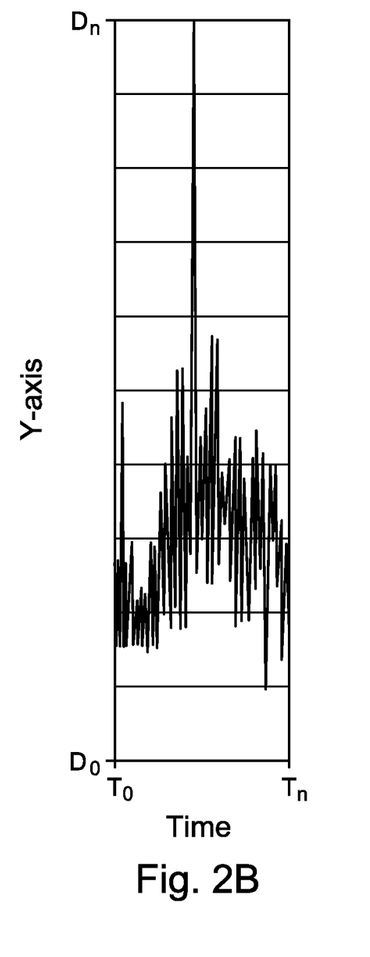
FIG. 2B illustrates an exemplary low density rimlier plotted along a time sequence.
Figure 2C:
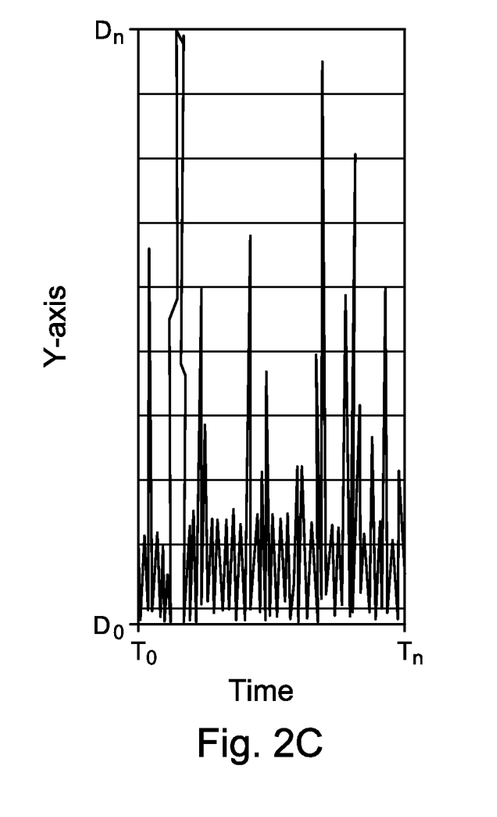
FIG. 2C illustrates an exemplary high density rimlier plotted along a time sequence.
Figure 2D:
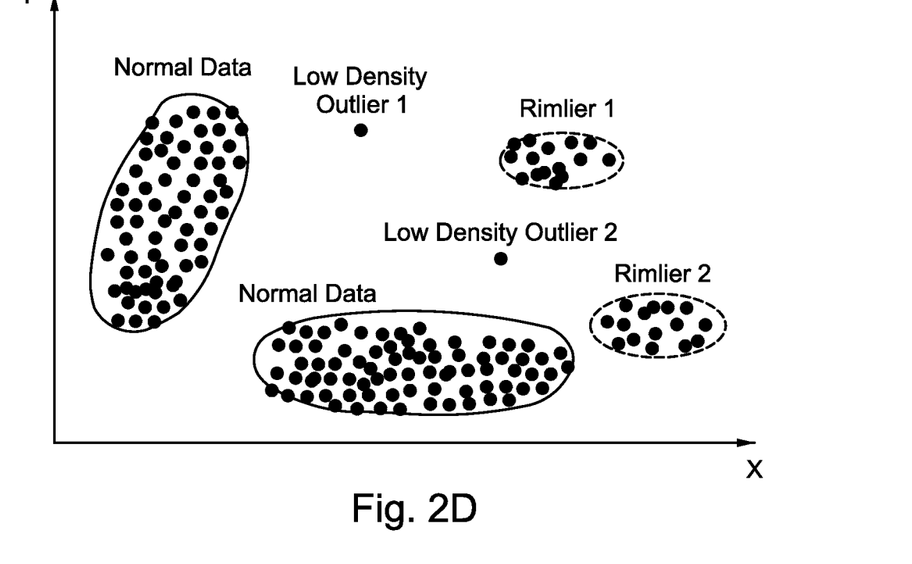
FIG. 2D illustrates a data distribution of normal data, low density outliers and rimliers according to an exemplary embodiment of the present invention.

If, at block 210, rimlier analysis engine 110 logically determines a "No," the algorithm loops back to block 204 and begins again. If, however, rimlier analysis engine 110 determines a "Yes" (i.e., high density outlier clusters exist), these high density clusters will be flagged as rimliers at block 212. To illustrate this point, FIG. 2B shows an exemplary time sequence distribution $T_0 \ldots T_n$ of a low density cluster having only a few data spikes (outliers) corresponding to one or more real-time downhole assembly measurements $D_0 \ldots D_n$ (stand-pipe pressure, torque, weight on bit, bit rotation speed, etc., for example), while FIG. 2C shows a similar distribution of a high density cluster having multiple data spikes (outliers), as opposed to normal data points. FIG. 2D shows an exemplary distribution of low and high density outliers along the X,Y planes. Here, normal and outlier data points have been clustered and plotted by rimlier analysis engine 110. It is then found that the extracted dataset contained low density outliers 1 and 2 and high density outlier clusters, or rimliers, 1 and 2. Accordingly, at block 212, rimlier analysis engine 110 then flags high density outliers 1 and 2 as rimliers 1 and 2.

At block 214, rimlier analysis engine 110, using data analysis module 114, analyzes the rimliers to identify those variables which can be used to model downhole events. To accomplish this, rimlier analysis engine 110 may utilize a variety of multivariate statistical techniques such as, for example, least squares regression, neural networks, fuzzy or hybrid neuro-fuzzy, rule-based, case-based or decision tree techniques. As will be understood by those ordinarily skilled in the art having the benefit of this disclosure, utilizing such techniques, the present invention interpolates based upon principles of physics, existing statistical models, historical data, and recent behavior to determine the likely consequences or projected future of the well and its component based upon presence of the rimliers. As previously described, presence of the rimliers may indicate, for example, the possible deterioration of the bit performance leading to insert failure or possible costly remediation trips.

Figure 2E:
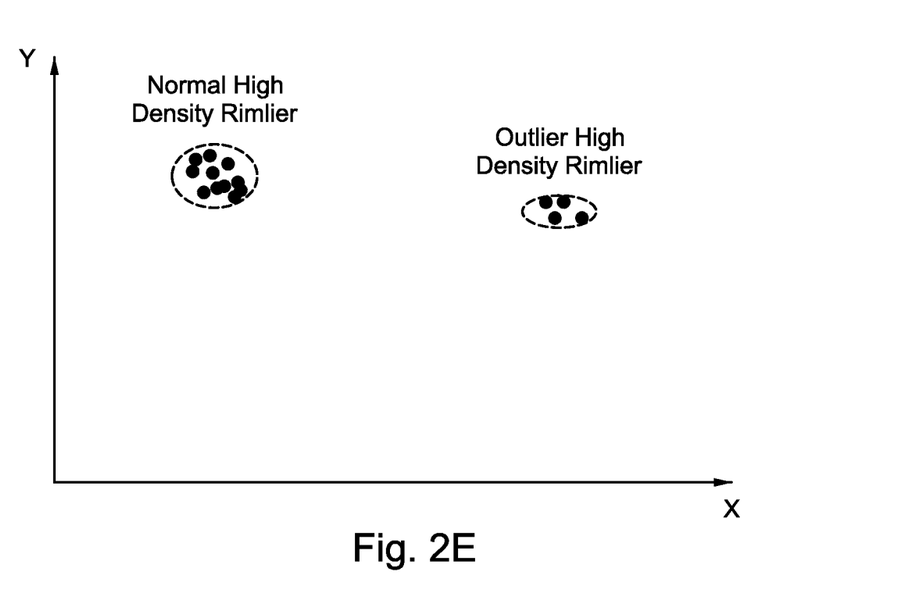
FIG. 2E illustrates a data distribution of normal and outlier high density rimliers according to an exemplary embodiment of the present invention.

In a first exemplary methodology, rimlier analysis engine 110 may perform a micro-analysis of a single rimlier at block 214(a). Here, referring to FIG. 2E, rimlier analysis engine 110 further clusters the single rimlier into a normal high density rimlier and outlier high density rimlier. Rimlier analysis engine 110 then analyzes the outlier high density rimlier to determine if further micro-clustering is possible, while the normal high density outlier 1 is discarded (since it really is not a significant rimlier). If a given micro-cluster is far away from other clusters along the plot, this may indicate there are outliers within the rimlier. For example, there may be multiple negative rotational speeds which exceed the mechanical threshold for the drill string. As such, rimlier analysis engine 110 may continue the micro-clustering of subsequent rimliers until those rimliers that are the specific signatures of a possible undesirable event are isolated and identified. Thus, this option allows rimlier analysis engine 110 to eliminate unnecessary outliers within the rimlier or to identify additional clusters useful in event prediction and detection. This algorithm continues iteratively until, ultimately, at block 216, rimlier analysis engine 110 models downhole events.

In a second exemplary methodology, rimlier analysis engine 110 may perform a macro-analysis of multiple rimliers at block 214(b). Among other things, the macro-analysis can be used to study the pattern of the rimliers so that events can be predicted. In addition, rimlier analysis engine 110 may also analyze the rimliers to identify patterns, variances, trends, classes, various responses, etc., as will be understood by those ordinarily skilled in the art having the benefit of this disclosure. Entropy techniques, as will be understood by those ordinarily skilled in the art having the benefit of this disclosure, can be utilized to predict, for example, tool failures, vibration—lateral or radial etc. In addition, rimlier analysis engine 110 may utilize entropy to study the homogeneity of the rimliers, which will ensure the rimliers have uniform data over a given period of time. The entropy of homogeneous data is zero, while the entropy of the rimliers must be calculated.

Figure 2F:
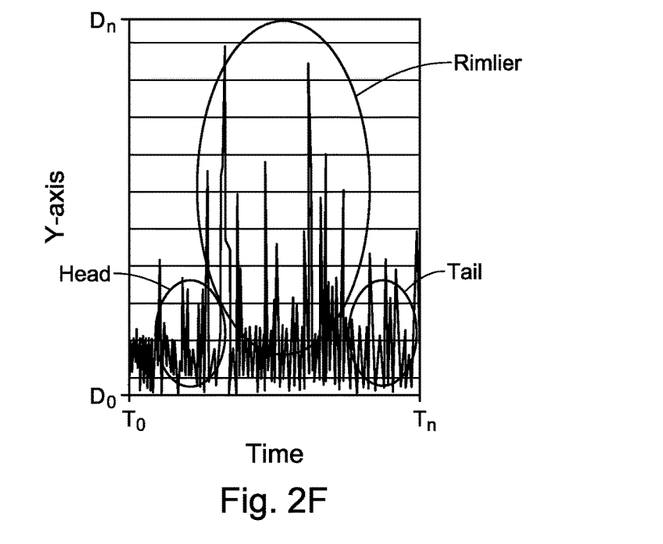
FIG. 2F illustrates a head-rimlier-tail distribution plotted along a time sequence according to an exemplary embodiment of the present invention.

Referring to FIG. 2F, a time series distribution of a head-rimlier-tail is plotted to further illustrate this exemplary methodology. To perform the entropy analysis, rimlier analysis engine 110 must determine the relative entropy between the head data and the rimlier data and the tail data and rimlier data using the following:

$$\text{Entropy is defined as } E = \Sigma - p(x)\log(x) \qquad \text{Eq. (1)}$$

where p(x) is the probability of x.

Here, rimlier analysis engine 110 first utilizes a clustering technique to detect and add rimliers, as previously described. In addition to clustering, other techniques may be utilized to detect and add rimliers such as, for example, rule-based, density-based, decomposition, SVM, neural network, etc., as will be understood by ordinarily skilled persons having the benefit of this disclosure. Second, rimlier analysis engine 110 calculates the Head and Tail for the rimlier factors. Head Rimlier Factor is defined as the ratio of the entropy of the head to the rimlier data, as shown below:

$$\text{Head Rimlier Factor} = \frac{E_h}{E_r} = \frac{\Sigma - p_h(x)\log(x)}{\Sigma - p_r(x)\log(x)} \qquad \text{Eq. (2)}$$

Tail Rimlier Factor is defined as the ratio of the entropy of the tail to the rimlier data, and is calculated by rimlier analysis engine 110 as follows:

$$\text{Tail Rimlier Factor} = \frac{E_t}{E_r} = \frac{\Sigma - p_t(x)\log(x)}{\Sigma - p_r(x)\log(x)} \qquad \text{Eq. (3)}$$

Once rimlier analysis engine 110 calculates the ratios (i.e., the Head and Tail Rimlier Factors), they are then used by rimlier analysis engine 110 to quantify and predict, or model, downhole events at block 216. For example, an increase in the rimlier ratio or density beyond a defined threshold and, therefore, an increase in weight and significance, indicates a present or impending downhole event. However, if the rimlier ratio is decreasing, the problem is vanishing. In an alternative exemplary embodiment, rimlier analysis engine 110 may utilize this ratio for multiple clusters. Again, if the ratio begins to decrease, this indicates there are no downhole problems. However, if this this ratio starts increasing, it may result in a catastrophic failure. In such scenarios, at block 216, rimlier analysis engine 110 may transmit an alert signal via the user interface to alert the user based upon a predefined user threshold.

In other exemplary embodiments, rimlier analysis engine 110 may also compare this ratio against the mechanical or hydro mechanical specific energy to determine or predict the downhole problems. By performing this comparison, rimlier analysis engine 110 may determine how the energy in the downhole assembly is expended (i.e., if system efficiency is increasing or decreasing). For example, a decrease in system efficiency indicates the presence of present or future downhole event, while an increase in system efficiency indicates there are no issues. Accordingly, at block 216, such events are modeled by rimlier analysis engine 110, whereby the events are predicted and/or detected.

In certain exemplary embodiments, rimlier analysis engine 110 can also utilize entropy to cross-correlate with other data such as, for example, similar tool data at different depths, as well as gamma ray, resistivity and other measurements received from other tools in the drill string. Such data from other tools may be received in real-time or from database storage. Through cross-correlation of this data, rimlier analysis engine 110 may counter verify, eliminate or substantiate the results. For example, the erratic variation of the bit torque may be due to a change in the formation observed through the gamma ray log—not due to a bit teeth problem. In such an embodiment, the rimlier data lies within multidimensional space with several variables which are cross-correlated with gamma ray and other logs to determine whether certain events are due to alterable variables (flow rate, for example), which can be eliminated or avoided, or unalterable variables (formation, for example). Thereafter, at block 216, in addition to predicting and/or detecting events, rimlier analysis engine 110 may also determine whether certain events can be avoided.

Accordingly, based on the foregoing analysis, rimlier analysis engine 110 models wellbore events. In addition to certain sustained data points indicating downhole events, different trends, for example, may be used to indicate events. For example, analysis of the rimlier data may indicate that the drag in the string is increasing at the surface; however, the data may also reflect an increasing entropy trend indicating an future stuck pipe event. Similarly, string and bit teeth failure may also be detected, for example.

Rimlier analysis engine 110 may output the results in a variety of ways such as, for example, an earth model, plotted graph, two or three-dimensional image, etc., as would be understood by those ordinarily skilled in the art having the benefit of this disclosure. In this regard, visualization of data is an important feature of any data mining analysis. Once the dimension of the data is 3 or higher, human visualization of data becomes quite difficult. As such, certain exemplary embodiments of the present invention utilize Multidimensional Scaling ("MDS") at block 216 to enhance the analysis of WDMA system 100 with data visualization, as this technique reduces the dimension of the data for visualization purposes, as will be understood by those ordinarily skilled in the art having the benefit of this disclosure.

Figure 3:
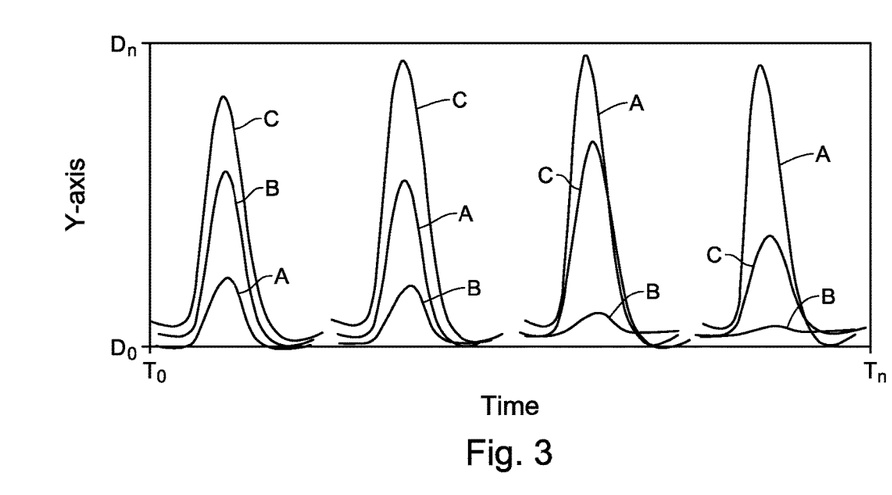
FIG. 3 illustrates measured while drilling variables and their influence with respect to time in accordance with an exemplary embodiment of the present invention.

Referring to FIG. 3, certain exemplary embodiments of the present invention may also utilize different distributions or spectral analysis to analyze the rimliers so that the influencing parameters for a given event can be determined. Such distribution analysis can be used to study the data in the frequency domain and is known in the art. In the example shown in FIG. 3, rimliers A, B and C are plotted to represent a drilling measured variable $D_0 \ldots D_n$ and its influence on rimliers A, B, and C with respect to time $T_0 \ldots T_n$. In the alternative, the distribution or spectral analysis may be based upon some other variable such as, for example, depth. In another embodiment, heat maps (not shown) of variables can also be displayed to indicate danger events and their increased presence. In yet another exemplary embodiment, the rimlier analysis engine 110 may utilized the predicted failure events to determine or estimate non-productive time by translating such events accordingly, as would be understood by those ordinarily skilled in the art having the benefit of this disclosure.

In yet another exemplary embodiment, rimlier data analysis system 100 may predict a drilling rate or bit life using data from a single well or multiple wells. Through utilization of one or more of the analysis methods described above, rimlier analysis engine 110 calculates adjustment factors between the actual and modeled rimlier values of drilling related data. Calculation of such adjustment factors may, for example, be conducted iteratively or algorithmically to match the actual data, as will be understood by those ordinarily skilled in the art having the benefit of this disclosure. For example, a calculated value of 100 and actual value of 110 has an adjustment factor of 1.1.

Nevertheless, once the adjustment factors are calculated, rimlier analysis engine 110 may determine the trend and assign a correlating weighting factor to perform forward modeling. For example, comparison of specific energy calculations to calculations of rock strength, either unconfined rock strength or confined rock strength enables continuous evaluation of drilling performance to identify limiters such as, for example, flounder points, in the drilling system, teeth wear or bit near failure. Here, based upon the comparison, rimlier analysis engine 110 determines the energy necessary to supply to the bit in order to breakdown the formation, thus ensuring bit life is used effectively.

Accordingly, in certain exemplary embodiments, rimlier analysis engine 110 may recommend drilling parameters to ensure optimal drilling efficiency and bit life. As downhole formation evaluation tools update and correct for formation variations that result in varying formation compressive strengths, rimlier analysis engine 110 may recalculate the bit wear and life variations accordingly. In such embodiments, rimlier data analysis system 100 receives real-time data from downhole sensors, as would be understood by those ordinarily skilled in the art having the benefit of this disclosure.

As described herein, exemplary embodiments of the present invention provide systems to data-mine and identify rimlier data to detect and/or prevent downhole events, thus providing valuable insight into drilling operations, production enhancement and well stimulation/completion. Since certain exemplary embodiments of the present invention only analyze the rimliers, a fast and efficient statistical process is provided which requires less storage space and processing power than prior art systems.

Moreover, the ability of the present invention to cluster downhole data coupled with analysis of only the rimliers will provide added insights into real-time or predicted events. As described herein, clustering high density rimlier data will enable detecting and/or prediction of events such as, for example, bit failure, tool failure due to vibration, etc. In addition, the present invention also determines whether certain predicted or detected events are alterable or unalterable. Furthermore, the present invention is also useful in its ability to presents the results in a simple, intuitive and easy to understand format that makes it a very efficient tool to predict and/or detect downhole events.

The foregoing methods and systems described herein are particularly useful in planning, altering and/or drilling wellbores. As described, the system analyses one or more rimliers to identify characteristics that may be used to predict and/or detect well events. Once identified, the detected/predicted events may then be presented visually via the user interface. This data can then be utilized to identify well equipment and develop a well workflow or stimulation plan. Thereafter, the wellbore is drilled, stimulated, altered and/or completed in accordance to those characteristics identified using the present invention.

Those of ordinary skill in the art will appreciate that the methods of the present invention may also be implemented dynamically. Thus, a well placement or stimulation plan may be updated in real-time based upon the output of the present invention. Also, after implementing the well placement or stimulation plan, the system of the invention may be utilized during the completion process on the fly or iteratively to determine optimal well trajectories, fracture initiation points and/or stimulation design as wellbore parameters change or are clarified or adjusted. In either case, the results of the dynamic calculations may be utilized to alter a previously implemented well placement or stimulation plan.

An exemplary methodology of the present invention provides a computer-implemented method to model downhole events, the method comprising extracting a dataset from a database, the dataset comprising normal wellbore data and outlier wellbore data, clustering a plurality of the outlier data to form a rimlier, analyzing the rimlier to determine those data variables within the rimlier that indicate a downhole event, and modeling the downhole event based upon the analysis of the rimlier. In another method, clustering the plurality of outlier data to form a rimlier further comprises clustering the plurality of outlier data into a plurality of clusters, segregating the plurality of clusters into a high density cluster and a low density cluster, and flagging those high density clusters as the rimlier. Yet another method further comprises removing corrupted data from the extracted dataset.

In another method, analyzing the rimlier further comprises segregating the rimlier into a normal high density rimlier and a outlier high density rimlier and analyzing the outlier high density rimlier to determine those data variables that indicate the downhole event. In yet another, clustering the plurality of the outlier data to form the rimlier further comprises forming a plurality of rimliers. In another, modeling the downhole event further comprises modeling an energy efficiency of a downhole assembly. Yet another method further comprises determining whether the modeled downhole event can be avoided. Another method further comprises producing an alert signal corresponding to the modeled downhole event. Yet another method further comprises displaying the modeled downhole event in the form of a tree or earth model. In yet another, a wellbore is drilled, completed or stimulated in accordance to the modeled downhole events.

Another exemplary embodiment of the present invention provides a system comprising processing circuitry to perform the methods described herein. Yet another exemplary embodiment of the present invention provides a computer program product comprising instructions which, when executed by at least one processor, causes the processor to perform the methods described herein.

Although various embodiments and methodologies have been shown and described, the invention is not limited to such embodiments and methodologies and will be understood to include all modifications and variations as would be apparent to one skilled in the art. For example, although described herein as utilizing rimlier data, exemplary embodiments of the present invention may also use normal data in conjunction with rimliers to detect or model downhole events. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. A computer-implemented method to model downhole events, the method comprising:
   extracting a dataset from a database, the dataset comprising normal wellbore data and outlier wellbore data;
   clustering a plurality of the outlier data into a plurality of clusters;
   segregating the plurality of clusters into a high density cluster and a low density cluster, wherein the high density clusters are utilized as a rimlier;
   analyzing the rimlier to determine data variables within the rimlier that indicate a downhole event, wherein the analyzing comprises:
   determining a Head Rimlier Factor as defined by:

$$\frac{E_h}{E_r} = \frac{\Sigma - p_h(x)\log(x)}{\Sigma - p_r(x)\log(x)};$$

and
   determining a Tail Rimlier Factor as defined by:

$$\frac{Et}{E_r} = \frac{\Sigma - p_t(x)\log(x)}{\Sigma - p_r(x)\log(x)},$$

wherein $E_h$ is entropy of head data, $p_h$ is probability of the head data, $E_r$ is entropy of rimlier data, $p_r$ is probability of the rimlier data, $E_t$ is entropy of tail data, and $p_t$ is probability of the tail data, wherein the Head Rimlier Factor and the Tail Rimlier Factor are utilized to determine the data variables indicating the downhole event; and modeling the downhole event based upon the analysis of the rimlier, wherein a wellbore is drilled, completed or stimulated in accordance to the modeled downhole events.

2. A computer-implemented method as defined in claim 1, further comprising removing corrupted data from the extracted dataset.

3. A computer-implemented method as defined in claim 1, wherein analyzing the rimlier further comprises:

segregating the rimlier into a normal high density rimlier and an outlier high density rimlier; and analyzing the outlier high density rimlier to determine the data variables that indicate the downhole event.

4. A computer-implemented method as defined in claim 1, wherein clustering the plurality of the outlier data further comprises forming a plurality of rimliers.

5. A computer-implemented method as defined in claim 4, wherein modeling the downhole event further comprises modeling an energy efficiency of a downhole assembly.

6. A computer-implemented method as defined in claim 1, further comprising determining whether the modeled downhole event can be avoided.

7. A computer-implemented method as defined in claim 1, further comprising producing an alert signal corresponding to the modeled downhole event.

8. A computer-implemented method as defined in claim 1, further comprising displaying the modeled downhole event in the form of a tree or earth model.

9. A computer-implemented method as defined in claim 4, wherein analyzing the plurality of rimliers further comprises determining a pattern across the plurality of rimliers, wherein the downhole events are modeled based upon the determined patterns.

10. A system comprising processing circuitry to perform the method comprising:

extracting a dataset from a database, the dataset comprising normal wellbore data and outlier wellbore data;

clustering a plurality of the outlier data into a plurality of clusters;

segregating the plurality of clusters into a high density cluster and a low density cluster, wherein the high density clusters are utilized as a rimlier;

analyzing the rimlier to determine data variables within the rimlier that indicate a downhole event, wherein the analyzing comprises:

determining a Head Rimlier Factor as defined by:

$$\frac{E_h}{E_r} = \frac{\Sigma - p_h(x)\log(x)}{\Sigma - p_r(x)\log(x)};$$

and
determining a Tail Rimlier Factor as defined by:

$$\frac{Et}{E_r} = \frac{\Sigma - p_t(x)\log(x)}{\Sigma - p_r(x)\log(x)},$$

wherein $E_h$ is entropy of head data, $p_h$ is probability of the head data, $E_r$ is entropy of rimlier data, $p_r$ is probability of the rimlier data, $E_l$ is entropy of tail data, and $p_l$ is probability of the tail data, wherein the Head Rimlier Factor and the Tail Rimlier Factor are utilized to determine the data variables indicating the downhole event; and modeling the downhole event based upon the analysis of the rimlier, wherein a wellbore is drilled, completed or stimulated in accordance to the modeled downhole events.

11. A system as defined in claim 10, further comprising removing corrupted data from the extracted dataset.

12. A system as defined in claim 10, wherein analyzing the rimlier further comprises:

segregating the rimlier into a normal high density rimlier and an outlier high density rimlier; and analyzing the outlier high density rimlier to determine the data variables that indicate the downhole event.

13. A system as defined in claim 10, wherein clustering the plurality of the outlier data further comprises forming, a plurality of rimliers.

14. A system as defined in claim 10, wherein modeling the downhole event further comprises modeling an energy efficiency of a downhole assembly.

15. A system as defined in claim 10, further comprising determining whether the modeled downhole event can be avoided.

16. A system as defined in claim 10, further comprising producing an alert signal corresponding to the modeled downhole event.

17. A system as defined in claim 10, further comprising displaying the modeled downhole event in the form of a tree or earth model.

18. A system as defined in claim 13, wherein analyzing the plurality of rimliers further comprises determining a pattern across the plurality of rimliers, wherein the downhole events are modeled based upon the determined patterns.

19. A non-transitory computer-readable medium comprising instructions which, when executed by at least one processor, causes the processor to perform the method comprising:

extracting a dataset from a database, the dataset comprising normal wellbore data and outlier wellbore data;

clustering a plurality of the outlier data into a plurality of clusters;

segregating the plurality of clusters into a high density cluster and a low density cluster, wherein the high density clusters are utilized as a rimlier;

analyzing the rimlier to determine data variables within the rimlier that indicate a downhole event, wherein the analyzing comprises:

determining a Head Rimlier Factor as defined by:

$$\frac{E_h}{E_r} = \frac{\Sigma - p_h(x)\log(x)}{\Sigma - p_r(x)\log(x)};$$

and
determining a Tail Rimlier Factor as defined by:

$$\frac{Et}{E_r} = \frac{\Sigma - p_t(x)\log(x)}{\Sigma - p_r(x)\log(x)},$$

wherein $E_h$ is entropy of head data, $p_h$ is probability of the head data, $E_r$ is entropy of dinner data, $p_r$ is probability of the rimlier data, $E_t$ is entropy of tail data, and $p_t$ is probability of the tail data, wherein the Head Rimlier Factor and the Tail Rimlier Factor are utilized to determine the data variables indicating the downhole event; and modeling the downhole event based upon the analysis of the rimlier, wherein a wellbore is drilled, completed or stimulated in accordance to the modeled downhole events.

20. A non-transitory computer-readable medium as defined in claim 19, further comprising removing corrupted data from the extracted dataset.

21. A non-transitory computer-readable medium as defined in claim 19, wherein analyzing the rimlier further comprises:
   segregating the rimlier into a normal high density rimlier and an outlier high density rimlier; and
   analyzing the outlier high density rimlier to determine the data variables that indicate the downhole event.

22. A non-transitory computer-readable medium as defined in claim 19, wherein clustering the plurality of the outlier data further comprises forming a plurality of rimliers.

23. A non-transitory computer-readable medium as defined in claim 19, wherein modeling the downhole event further comprises modeling an energy efficiency of a downhole assembly.

24. A non-transitory computer-readable medium as defined in claim 19, further comprising determining whether the modeled downhole event can be avoided.

25. A non-transitory computer-readable medium as defined in claim 19, further comprising producing an alert signal corresponding to the modeled downhole event.

26. A non-transitory computer-readable medium as defined in claim 19, further comprising displaying the modeled downhole event in the form of a tree or earth model.

27. A non-transitory computer-readable medium as defined in claim 19, wherein analyzing the plurality of rimliers further comprises determining a pattern across the plurality of rimliers, wherein the downhole events are modeled based upon the determined patterns.

* * * * *